United States Patent
Albassam et al.

(10) Patent No.: US 12,031,430 B2
(45) Date of Patent: Jul. 9, 2024

(54) MEASURING DRILLING FLUID pH WITH SMART POLYMERS

(71) Applicant: Saudi Arabian Oil Company, Dhahran (SA)

(72) Inventors: Mohammed Albassam, Al-Khobar (SA); Arturo Magana Mora, Dhahran (SA); Chinthaka Pasan Gooneratne, Dhahran (SA); Mohammad Aljubran, Dhahran (SA); Peter Boul, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 9 days.

(21) Appl. No.: 17/959,408

(22) Filed: Oct. 4, 2022

(65) Prior Publication Data
US 2024/0110476 A1    Apr. 4, 2024

(51) Int. Cl.
E21B 49/08    (2006.01)
C09K 8/24    (2006.01)
G01N 33/24    (2006.01)

(52) U.S. Cl.
CPC ............ *E21B 49/0875* (2020.05); *C09K 8/24* (2013.01); *G01N 33/24* (2013.01)

(58) Field of Classification Search
CPC ...... E21B 49/0875; E21B 17/00; E21B 44/00; E21B 41/0085; E21B 47/01; E21B 47/12; E21B 2200/20
See application file for complete search history.

(56) References Cited

U.S. PATENT DOCUMENTS

| | | |
|---|---|---|
| 10,905,636 B2 | 2/2021 | Musa et al. |
| 2019/0375978 A1 | 12/2019 | Shojaei et al. |
| 2019/0382519 A1 | 12/2019 | Musa et al. |

OTHER PUBLICATIONS

Bhattacharya et al., "Mechanical-Bending-Induced Fluorescence Enhancement in Plastically Flexible Crystals of a GFP Chromophore Analogue," Angewandte Chemie, Jul. 2020, 132(45):20050-20055, 6 pages.

Guo et al., "Fluorescence Chemosensors for Hydrogen Sulfide Detection in Biological Systems," Analyst, Mar. 2015, 140(6):1772-1786, 18 pages.

(Continued)

*Primary Examiner* — Zakiya W Bates
(74) *Attorney, Agent, or Firm* — Fish & Richardson P.C.

(57) ABSTRACT

Systems and methods include techniques for using smart polymers. Units of smart polymers with per-hydrogen (pH) sensitivity are inserted into drilling fluid pumped into a well during drilling. The smart polymers are configured to be triggered by hydrogen ion concentrations. An insertion timestamp associated with each unit is stored and indicates a time that each unit was inserted. Continuous images and observed characteristics of returning mud exiting through an annulus of the well and containing the units of smart polymer are captured by a camera positioned at a sensing location and linked to the monitoring system. An estimate of pH values at a drill bit of the drilling operation is determined using the continuous images, observed characteristics, and insertion timestamps, and based at least in part on executing image processing algorithms, machine-learning models, and deep-learning models. Changes to be made to drilling parameters are suggested.

7 Claims, 6 Drawing Sheets

(56) References Cited

OTHER PUBLICATIONS

Gustafson et al., "Design of Irreversible Optical Nanothermometers for Thermal Ablations," Chemical Communications, Jan. 2013, 49(7):680-682, 3 pages.
Han et al., "Fluorescent Indicators for Intracellular pH," Chem. Rev., May 2010, 110(5):2709-2728, 20 pages.
Herrmann, "Dynamic Combinatorial/Covalent Chemistry: A Tool to Read, Generate and Modulate the Bioactivity of Compounds and Compound Mixtures," Chemical Society Reviews, Mar. 2014, 43(6):1899-1933, 36 pages.
Li et al., "Dually emitting carbon docts as fluorescent probes for ratiometric fluorescent sensing of pH values, mercury(II), chloride and Cr(VI) via different mechanisms," Microchimica Acta, May 2019, 186(6):341, 10 pages.
Qu et al., "Polyethyleneimine-templated Ag nanoclusters: A new fluorescent and colorimetric platform for sensitive and selective sensing halide ions and high disturbance-tolerant recognitions of iodide and bromide in coexistence with chloride under condition of high ionic strength," Analytical Chemistry, Nov. 2012, 84(23):10373-10379, 7 pages.
Stefani et al., "Thermochromic Fluorophores and Their NIR Laser Induced Transformation," Chemistry of Materials, Dec. 2006, 18(26):6115-6120, 6 pages.
Tollan et al., "Irreversible Thermochromic Behavior in Gold and Silver Nanorod/Polymeric Ionic Liquid Nanocomposite Films," ACS Applied Materials & Interfaces, Feb. 2009, 1(2):348-352, 5 pages.
Yu et al., "Carbon-Dot-Based Ratiometric Fluorescent Sensor for Detecting Hydrogen Sulfide in Aqueous Media and inside Live Cells," Chemical Communications, Jan. 2013, 49(4):403-405, 3 pages.

PS-b-P4VP 402 poly(DEAEAM-r-NIPAM) 404

406

408

MEASURING DRILLING FLUID pH WITH SMART POLYMERS

TECHNICAL FIELD

The present disclosure applies to measuring and estimating conditions while drilling wells, e.g., oil wells.

BACKGROUND

In chemistry, potential of hydrogen (pH) is a quantitative measurement of the acidity or basicity of liquid solutions. The scale ranges from 0 to 14, where solutions with a pH less than 7 are acidic, solutions with a pH greater than 7 are basic, and solutions with a pH of 7 are neutral solutions. Monitoring drilling fluids' pH is important to ensure that the acidity of the fluid is within an expected range. Some of the additives used in drilling fluids require a certain range of pH values to function effectively. In addition, drilling with a fluid that has a low pH (acidic solution) can result in casing and drill pipe corrosion.

SUMMARY

The present disclosure describes techniques that can be used to estimate drilling fluid potential of hydrogen (pH) at a drill bit during a drilling operation through the use of smart polymers introduced into drilling fluid and photographed in returning drilling mud after exposure to downhole conditions. In some implementations, a computer-implemented method includes the following. Units of smart polymers with per-hydrogen (pH) sensitivity are inserted by a monitoring system into drilling fluid pumped into a well during a drilling operation. The smart polymers are configured to be triggered by hydrogen ion concentrations. An insertion timestamp associated with each unit is stored by the monitoring system. Each insertion timestamp indicates a time that each unit was inserted into the drilling fluid. Continuous images and observed characteristics of returning mud exiting through an annulus of the well and containing the units of smart polymer are captured by a camera positioned at a sensing location and linked to the monitoring system. An estimate of pH values at a drill bit of the drilling operation is determined by the monitoring system using the continuous images, the observed characteristics, and the insertion timestamps associated with each unit of smart polymer. Determining the estimate is based at least in part on executing image processing algorithms, machine-learning models, and deep-learning models. Changes to be made to drilling parameters for the drilling operation are suggested by the monitoring system based at least in part on the estimate of the pH values.

The previously described implementation is implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented method, the instructions stored on the non-transitory, computer-readable medium.

The subject matter described in this specification can be implemented in particular implementations, so as to realize one or more of the following advantages. Techniques of the present disclosure can be used in drilling operations related to shale instability, which is one of the main reasons for tight holes and stuck pipe incidents. In addition, shale instability can also result in a loss of circulation, which can then lead to well control incidents. The techniques can also aid in geothermal fluids kick detection. The techniques can also be used to overcome limitations with drilling fluid pH measurements. A full drilling fluid check with determination of pH is only performed twice a day at most. Such intermittent and unreliable measurements are not sufficient to provide the required inputs for near "real time" fluid checks and control. Moreover, the technologies incorporated in the present disclosure can take advantage of emerging technologies aligned with the fourth industrial revolution (4IR), such as automation, Internet of Things (IoT), artificial intelligence (AI) machine learning, and data analytics. Techniques can include the use of a camera at the shale shaker and the used of smart polymers to evaluate the drilling fluid's pH at different timestamps and locations to ensure the pH of the fluid is within the acceptable range for safe operations.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DESCRIPTION OF DRAWINGS

Like reference numbers and designations in the various drawings indicate like elements.

DETAILED DESCRIPTION

Figure 1:
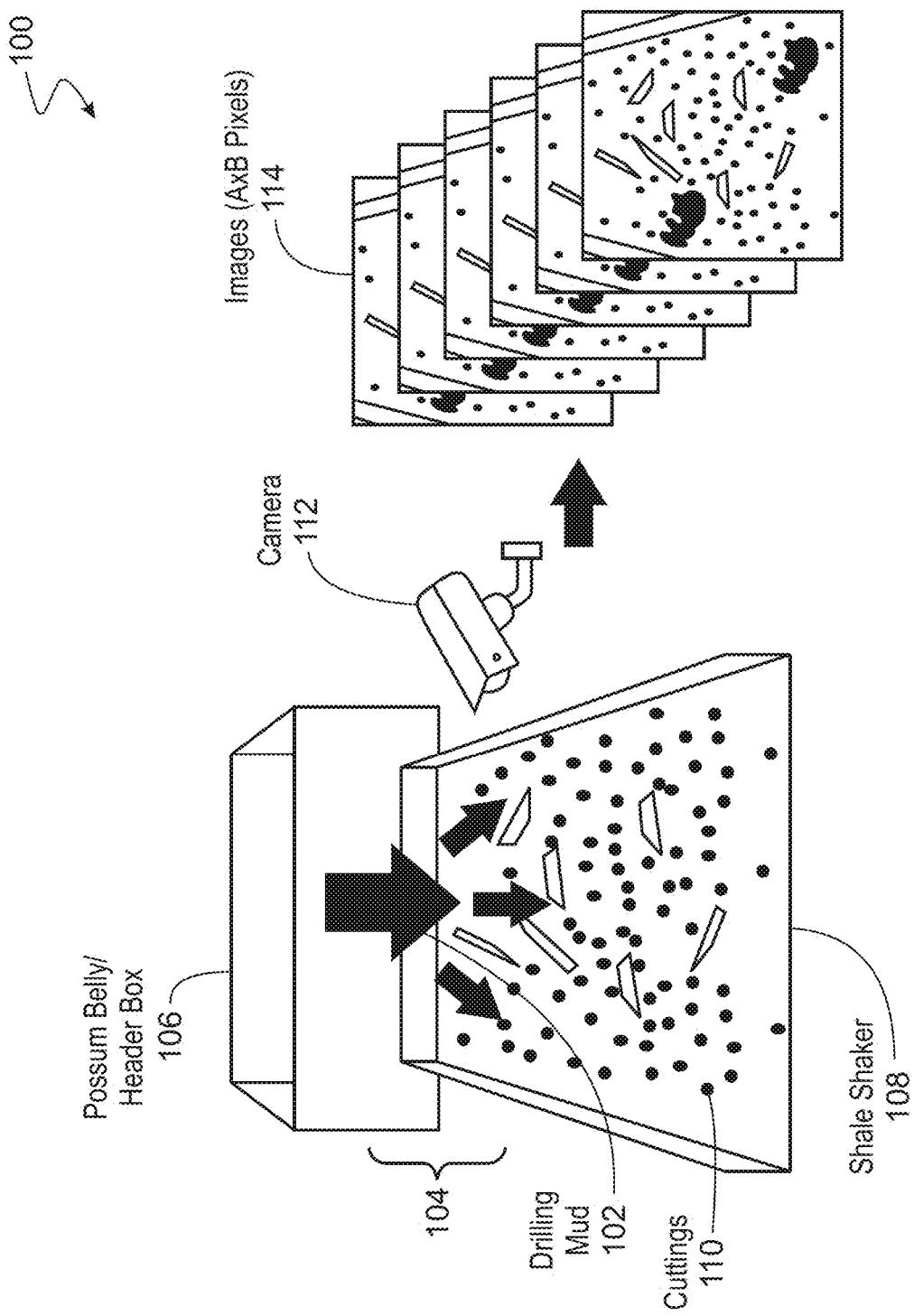
FIG. 1 is a plan view of an example of a shale shaker configuration, according to some implementations of the present disclosure.

The following detailed description describes techniques that can be used to estimate drilling fluid potential of hydrogen (pH) at a drill bit during a drilling operation. The estimate can be obtained through the use of smart polymers introduced into drilling fluid and photographed in returning drilling mud after exposure to downhole conditions. Various modifications, alterations, and permutations of the disclosed implementations can be made and will be readily apparent to those of ordinary skill in the art, and the general principles defined may be applied to other implementations and applications, without departing from the scope of the disclosure.

In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

The present disclosure describes a system in which pH is used as a trigger to change the color/intensity of smart polymers/fluids injected into a wellbore. The smart polymers/fluids can be subsequently captured by cameras recording frames/images that are analyzed automatically by computational models to detect pH in the wellbore. The system includes the use of smart polymers and an Internet of things (IoT) platform to be used on a drilling rig for estimating pH. The system can include: 1) smart, waterproof, high-resolution, wireless cameras, or any other image or vision sensor, including infrared, gamma ray, CT scan, x-ray, among others, for image/video capture of the shale shakers; 2) edge/fog computing hardware; and 3) software for image/video processing to transform discrete images to digital pH readings. Determining pH readings can provide advantages of: 1) avoiding drill pipe corrosion by over-acidic drilling fluid, and 2) identifying influxes by detecting sudden increases in pH levels of drilling mud. Drilling fluids are designed to have certain pH values prior to a drilling job, based on several parameters including lithology. During drilling, the fluid is expected to stay within a designed pH range. Techniques of the present disclosure can be used to detect values once they are out of the designed range.

Image data from the camera/vision sensors are expected to be primarily processed in continuous recording to capture the trends of the flow over time. The frames from the camera can be processed by the image processing algorithms and machine learning/deep learning (ML/DL) models 216 deployed in an edge/fog server 202. Image processing techniques can be used to detect the polymer intensity/color/light as well as to enhance the contrast and brightness of the frames as triggered by pH levels. The image processing techniques can include pixilation, image segmentation, intensity quantification, and supervised learning regression models (including ML and DL). Algorithms can be used to convert the images to arrays for subsequent translation to numerical values referring to discrete pH levels.

To develop and train ML models, smart polymer pills, for example, can be exposed to different pH concentrations in a lab. For example, certain pH levels can be applied, and images of the resulting polymers can be acquired. The images, when correlated to the actual applied pH concentrations, can then be used to train ML/DL models. Laboratory data can be required for the learning phase of the models, such as to represent the targets/labels. After the models are derived, the objective of the models can include predicting pH values of returning drilling fluid by using images captured and processed during real-time drilling operations.

Techniques can include the use of smart fluids/polymers and a camera recording the drilling mud returns at a shale shaker to measure the pH of drilling fluids in the wellbore. Smart polymers can include stimuli-responsive polymers that change properties according to the environment in which they are placed. Different stimuli include pressure, temperature, pH, and ionic strength, for example. Changes in properties can include shapes, chemical properties, and color. The present disclosure focuses on hydrogen ion concentration [$H^+$] as a trigger to change the color and intensity of smart polymers/fluids that are detected by the camera at the shale shaker.

The present disclosure describes a system that uses smart polymers that reacts to pH stimuli and an Internet of things (IoT) platform to be used on a drilling rig. The system includes: 1) smart, waterproof, high resolution, wireless cameras, or any other image or vision sensor, including infrared, gamma ray, CT scan, x-ray, among others, for image/video capture, 2) edge/fog computing hardware, and 3) software for image/video processing to transform discrete images to digital pH readings. The system can include advantages of: 1) avoiding drill pipe corrosion caused by acidic drilling fluid, and 2) identifying influxes by detecting sudden increases in pH levels of drilling mud.

A water-based drilling fluid is a mixture of water and other additives that provide weight, viscosity, and other characteristics to the fluid. A primary objective of using drilling fluids is to maintain wellbore stability by holding back formation pressure from entering the wellbore. Drilling fluids also aid in sealing permeable zones by forming a mud-cake on the wellbore wall that essentially reduces mud invasion to the formation. In addition, drilling fluids are used to remove cuttings from the wellbore to the surface and ensure proper hole cleaning to avoid stuck pipe incidents or even loss circulation.

Drilling with a fluid that has a low pH (acidic solution) can result in casing and drill pipe corrosion, which can cause leaks in the pipe. Casing is used to provide support/structure to the wellbore as well as to provide another layer of isolation behind the cement. Leaks in casing may result in bad zonal isolation where unwanted zones may communicate with each other. In addition, leaks in the drill pipe can lead to loss of drilling hydraulics, thus reducing the mud flow rate due to the leak.

Continuous monitoring of pH can aid in identifying if a kick has been taken and formation fluids enter the wellbore. Usually, drilling fluids' pH levels are between 9-11. An unplanned reduction or increase in pH can be the result of formation geo-fluid mixing with the current drilling fluid.

The continuous measurement of the pH value is an essential task to ensure a safe drilling environment. Consequently, the present disclosure describes a method that utilizes the smart fluids/polymers and a camera at the shale shaker to measure pH levels of the drilling fluid. Smart polymers are stimuli-responsive polymers that change properties according to the environment they are placed in. Different stimuli include temperature, pH, or ionic strength, among others. Change of properties includes changing shape, chemical properties, emitting light, or color. The present disclosure describes the use of hydrogen ion concentration [$H^+$] as a trigger to cause changes in the color/intensity of smart polymers/fluids. The changes can be automatically detected by computational models used to analyze frames obtained by the camera recording the shale shaker.

There are two types of stimuli-responsive polymers: reversible and irreversible. Irreversible polymers do not return to their natural state once the trigger has been eliminated from the environment. The present disclosure focuses on reversible polymers where properties can return back to their initial state. The use of reversible polymers can allow the system to measure pH at different times and locations in the fluid column.

The present disclosure addresses the current limitations with drilling fluid pH measurements. A full drilling fluid check with determination of pH is only performed twice a day at most. Such intermittent and unreliable measurements are not sufficient to provide the required inputs for near "real-time" fluid checks and control. These near real-time pH checks will ensure that the drilling fluid remains in the required pH range window for it to be effective. Additionally, the automatic measurement of pH allows for detecting sudden changes induced by influxes.

In the methods described in the present disclosure, the smart polymers are designed to be pumped with the drilling fluid as pills. For example, the pills can be pumped with the drilling mud at different intervals (e.g., every 1/3/5 minutes) or could be pumped every one stand (i.e., every 90 ft.). These "pH polymers" are designed to be triggered by hydrogen ion [$H^+$] concentration. The pH-responsive polymers change properties as a function of the [$H^+$] concentration in the environment applied. As the pill exits the well through the annulus, the camera at the shale shaker captures continuous images of the returning mud and uses image processing algorithms as well as machine-learning (ML)/deep-learning (DL) models to predict/estimate pH values.

FIG. 1 is a plan view of an example of a shale shaker configuration 100, according to some implementations of the present disclosure. Drilling mud flow 102 direction is represented by arrows 104. The mud enters a solids control process from a possum belly/header box 106. In this example, gravity feeds the mud into the vibrating basket of a shale shaker 108, loaded with course and fine mesh screens designed to sort the solids (e.g., cuttings 110) from the liquid phase. The mud moves from top to bottom, as shown in FIG. 1, through a motion caused by shaker basket vibration. As the drilling mud travels, the vibrational impact with the screen causes liquid/solid separation and/or drying. Upon discharge at the bottom of the shale shaker 108, the solids are discarded (as shown) while the liquid (and fine solids, depending on screen size) pass into the sump tank for further treatment and ultimate recycling for re-pumping downhole. A camera 112 is used to capture images 114, e.g., of dimension size A×B. The images 114 are processed by image processing algorithms and ML to convert analog data (e.g., intensity, color, and light) to digitized numerical pH value. Vision sensing can occur at multiple locations using multiple cameras, for example, at solids discharge from one or more of the shale shaker, centrifuges, de-sanders, de-silters, and locations using other solids control technologies. However, the present disclosure focuses on the shale shaker, with surface screening of solids in a load and discharge configuration as shown in FIG. 1.

The camera at the shale shaker along with hydrogen ion sensitive polymers offer a new technique for measuring pH. The novelty of the present disclosure is not in the polymer formulation as these are well established in the literature and science. The novelty of the present disclosure comes in using these hydrogen ion-responsive polymers to measure returning drilling fluids' pH values in the oil and gas industry. In addition, the present disclosure describes the implementation of ML/DL models that are capable of converting digital numerical pH values using image data. Consequently, the methods described in the present disclosure have the application of continuous measurements of drilling fluids pH value (FIG. 2).

Figure 2:
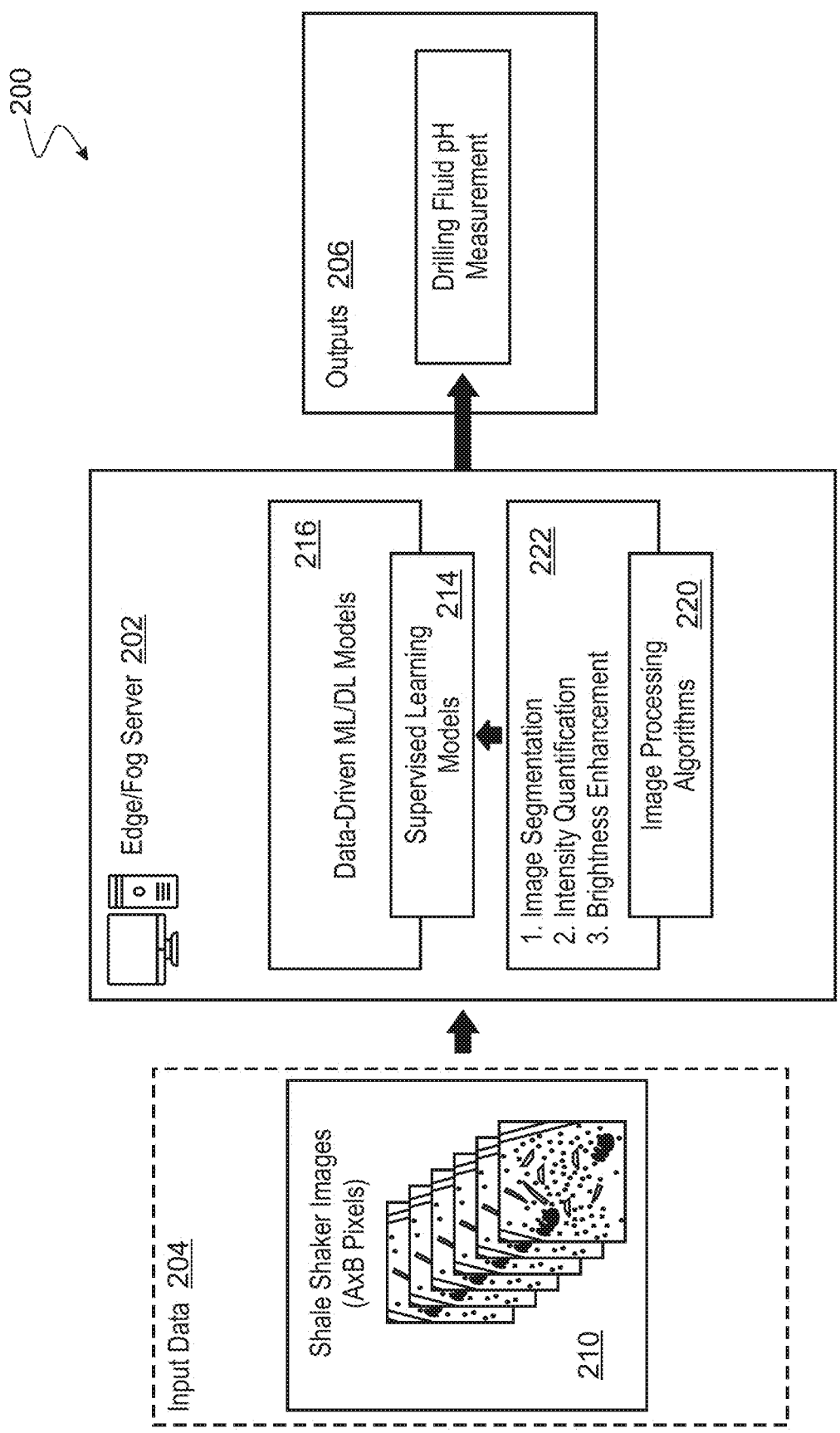
FIG. 2 is a drawing showing an example of inputs and outputs of a system for measuring drilling fluid potential of hydrogen (pH), according to some implementations of the present disclosure.

FIG. 2 is a drawing showing an example of inputs and outputs of a system 200 for measuring drilling fluid pH, according to some implementations of the present disclosure. The system 200 includes an edge/fog server 202 that processes input data 204 for the system 200 and generates outputs 206.

The input data 204 can include image data (e.g., shale shaker images 210). The edge/dog server 202 can use various models, including supervised learning models 214, which can serve as inputs to data-driven ML/DL models 216. The supervised learning models 214 can use as input outputs of image processing algorithms 220 that can perform functions 222 including image segmentations, intensity quantification, and brightness enhancement.

Image data from the camera/vision sensors are expected to be primarily processed in continuous recording to capture the trends of the flow over time. Frames from the camera can be processed by the image processing algorithms and ML/DL models deployed in the edge/fog server 202. The methods described in the present disclosure can use a set of image processing techniques to detect the polymer intensity/color/light in the frame as well as to enhance the contrast and brightness of the frames. The image processing techniques can include pixilation, image segmentation, intensity quantification, and supervised learning models (including ML and DL). Algorithms can be used to convert the images to arrays that can be later translated to digitize measurements of drilling fluid pH.

The numerical representation of the intensities of the polymers mixed with the fluid observed at the shale shakers can be used directly to estimate pH values. For instance, a simple logistic regression model may be used as follows:

$$pH=\beta \times \max(\text{pixel intensity}) \quad (1)$$

where β refers to the coefficient learned by the regression model, and max (pixel intensity) refers to the pixel with the highest intensity values in a frame, respectively. This pixel with the highest intensity refers to the highest polymer activation. pH refers to the pH values as measured in the laboratory. A linear regression, as a supervised learning model, can learn this relationship by observing multiple samples S with their respective target labels (H2S).

However, relying on the value of a single pixel intensity may not provide enough accuracy. Consequently, supervised learning DL models, such as convolutional neural networks (CNN) and auto encoder neural networks (AE-NN), among others, can be derived from the frames to classify the observed polymer intensity/color in the images. These models can consider the set of polymer intensities in the entire frame. Additional image processing algorithms can be used to crop the image, increase the brightness, or optionally select only a region of the image (image segmentation). The processed images can then be fed into DL models to automatically extract abstract features from the frames that can be linked to the hydrogen ion [$H^+$] as a target. In supervised learning, each frame containing the set of intensities observed from the smart polymer can be assigned a label (pH value) to train the regression DL model, as shown in FIG. 3.

To label the data (frames with their respective label), the smart polymer pills can be exposed to different hydrogen ion [$H^+$] concentrations in the lab, and the values can be recorded using a pH measurement tool kit. Certain pH values can be applied, and images of the resulting polymers can be acquired. These images along with the actual applied pH values can then be used to train the machine model. Notably, the laboratory data can be required for the learning phase of the model, as these data represent the targets/labels. After the model is derived, the objective of the model is to predict these values using the images.

Figure 3:
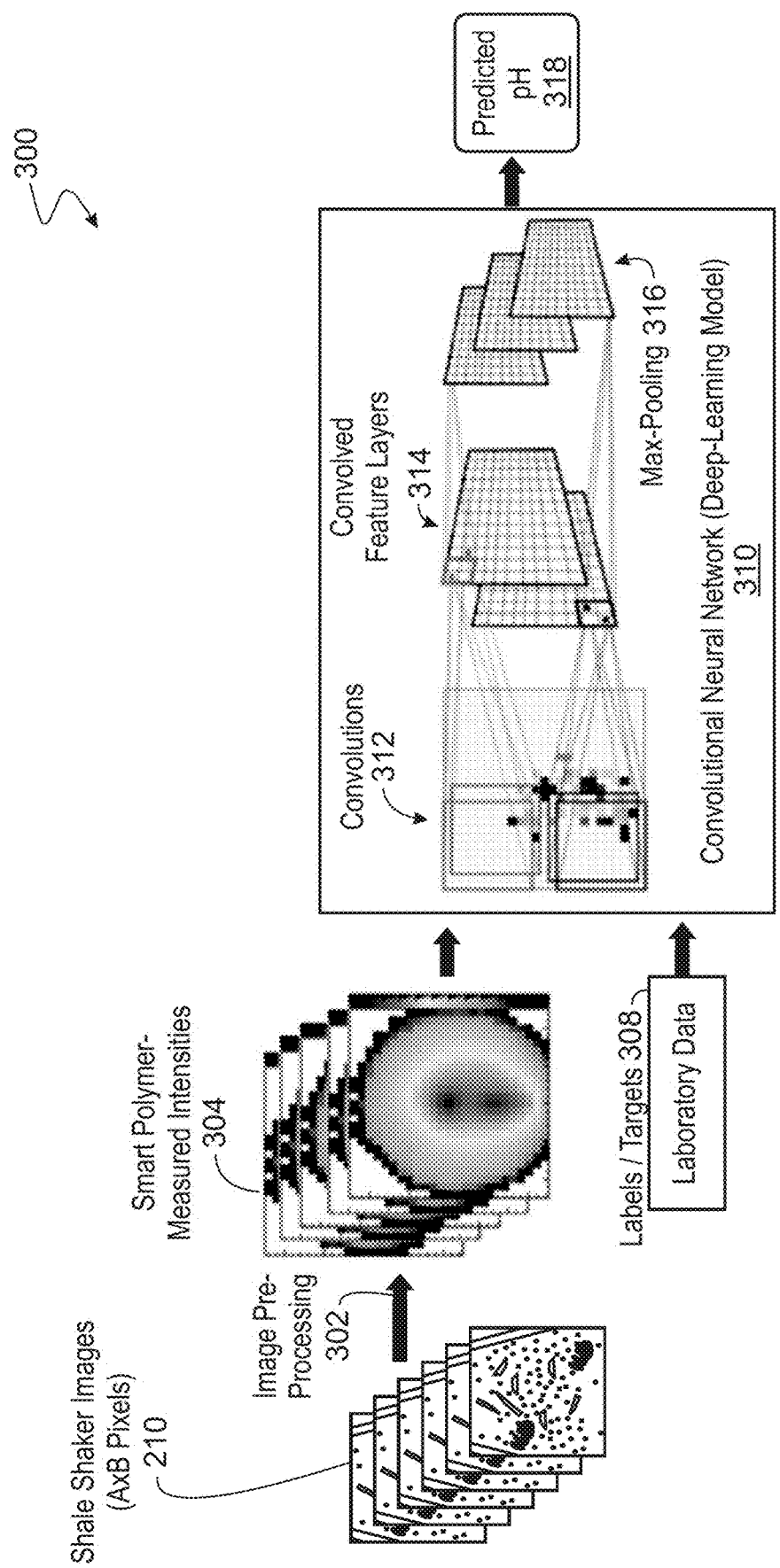
FIG. 3 is a diagram showing an example of a supervised learning method to predict/estimate the pH value, according to some implementations of the present disclosure.

FIG. 3 is a diagram showing an example of a supervised learning method 300 to predict/estimate the pH value, according to some implementations of the present disclosure. The supervised learning method 300 can be used as initial input for the shale shaker images 210. Image pre-processing 302 performed on the shale shaker images 210 can create smart polymer measured intensities 304. Labels/targets 308, along with the smart polymer measured intensities 304, can serve as inputs to a Convolutional Neural Network (CNN) (e.g., deep learning model) 310. Convolutions 312 can be used to create convolved feature layers 314 from which max-pooling 316 is performed. Output of the CNN 310 is a predicted pH 318.

Chemical Sensor

FIGS. 4A-4D collectively show examples of pH dual-responsive particles 402-408, according to some implementations of the present disclosure. Drilling muds laden with temperature and pH dual-responsive shape-switchable polystyrene-b-poly(4-vinylpyri-dine) (PS-b-P4VP) particles offer the possibility of showing a pH responsive fluorescence emission. The fluorescence emission can be recorded in real time with a standard CCD camera. A random copolymer of N-(2-(diethylamino)ethyl)acrylamide (DEAEAM) and N-isopropy-lacrylamide (NIPAM) (poly(DEAEAM-r-NIPAM 408)) can be utilized with PS-b-P4VP as a responsive polymeric surfactant. The purpose of this surfactant is to tune the pH range of the optically active pH sensitive PS-b-P4VP polymer.

Figure 4A:
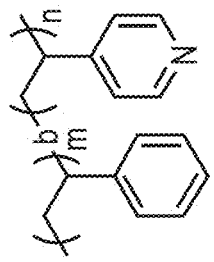
FIGS. 4A-4D collectively show examples of pH dual-responsive particles, according to some implementations of the present disclosure.
Figure 4B:
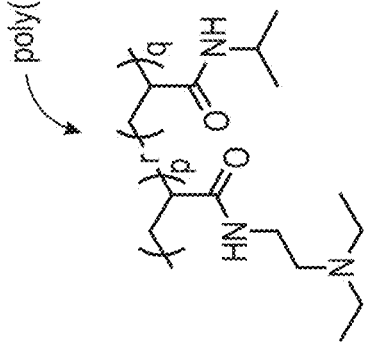
Figure 4C:
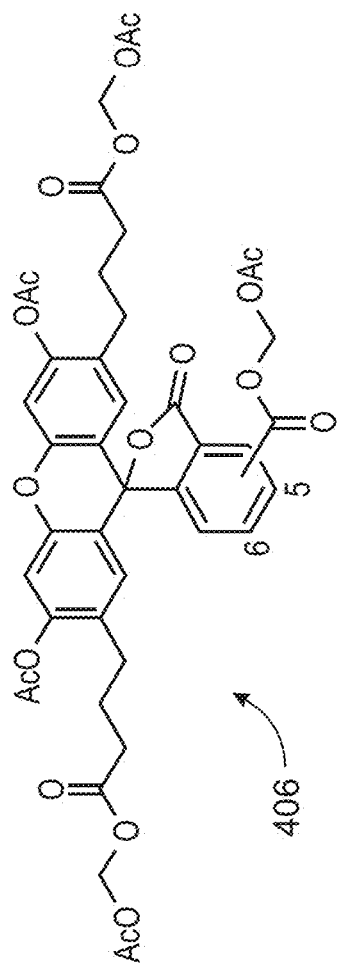
Figure 4D:
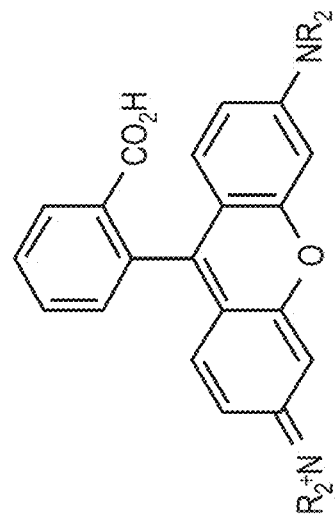

FIG. 4A shows 2',7'-bis-(2-carboxypropyl)-5-(and-6)-carboxyfluorescein. FIG. 4B shows rhodamine. Other possibilities for polymers which display this kind of pH sensitivity for determining the pH of drilling muds can include fluorescein or fluorescein derivatives (e.g., derivatives of 2',7'-bis-(2-carboxypropyl)-5-(and-6)-carboxyfluorescein), rhodamine or rhodamine derivatives, benxoxathines, and phthalonitriles).

Figure 5:
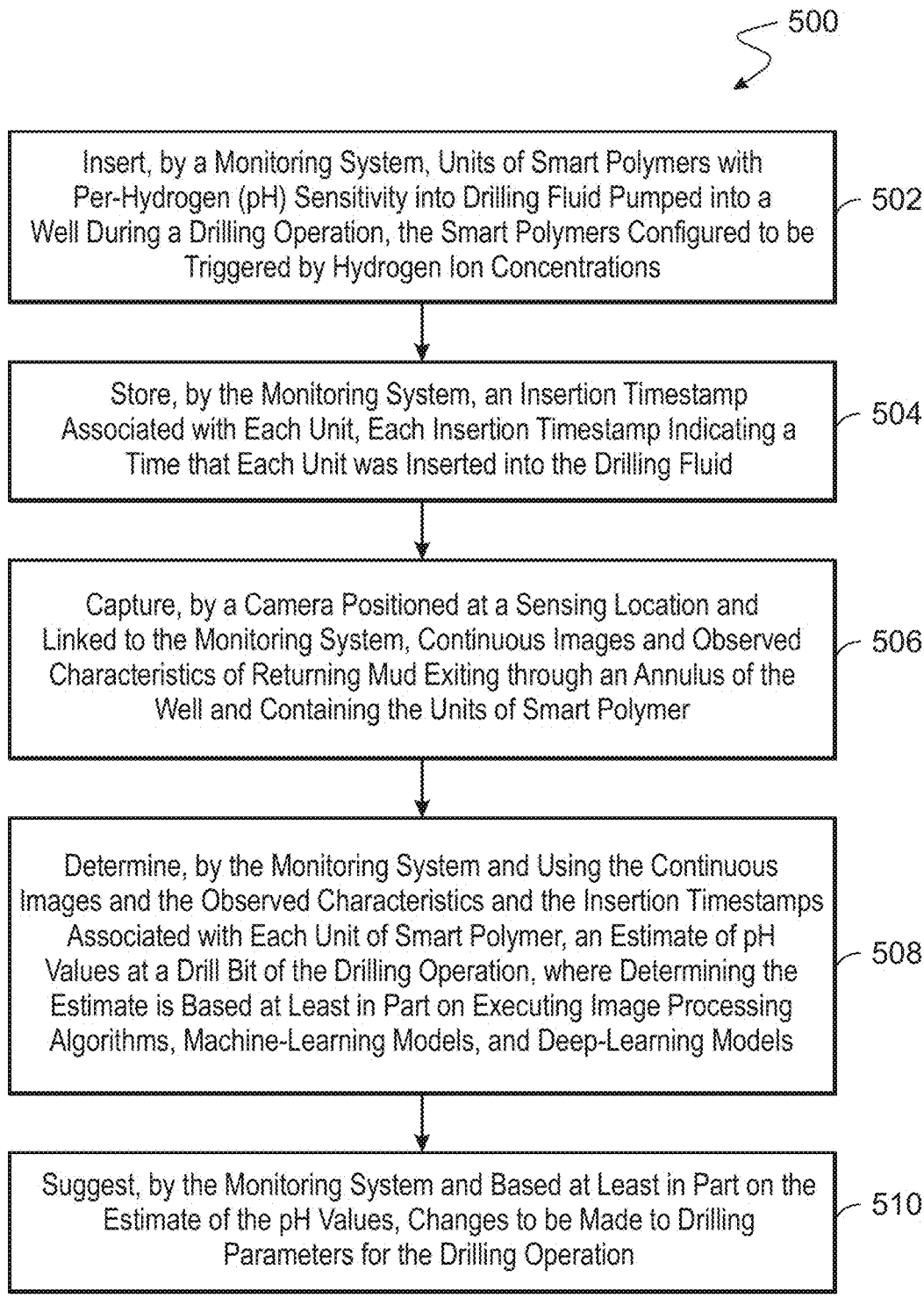
FIG. 5 is a flowchart of an example of a method used for estimating pH at a drill bit during a drilling operation through the use of smart polymers introduced into drilling fluid and photographed in returning drilling mud after exposure to downhole conditions, according to some implementations of the present disclosure.

FIG. 5 is a flowchart of an example of a method 500 used for estimating pH at a drill bit during a drilling operation through the use of smart polymers introduced into drilling fluid and photographed in returning drilling mud after exposure to downhole conditions, according to some implementations of the present disclosure. For clarity of presentation, the description that follows generally describes method 500 in the context of the other figures in this description. However, it will be understood that method 500 can be performed, for example, by any suitable system, environment, software, and hardware, or a combination of systems, environments, software, and hardware, as appropriate. In some implementations, various steps of method 500 can be run in parallel, in combination, in loops, or in any order.

At 502, units of smart polymers with per-hydrogen (pH) sensitivity are inserted by a monitoring system into drilling fluid pumped into a well during a drilling operation. The smart polymers are configured to be triggered by hydrogen ion concentrations. The units of smart polymers can have a pill shape, for example. Pills of various sizes and shapes can be used, and may depend on the types of geology or expected drilling conditions. The units of smart polymers can be pumped into the drilling fluid at different intervals (e.g., every one, three, or five minutes) or can be pumped every one stand (e.g., every 90 feet). The units of smart polymers can be configured to change properties as a function of exposure to different hydrogen ion [$H^+$] concentrations applied to the units of smart polymers by downhole conditions. From 502, method 500 proceeds to 504.

At 504, an insertion timestamp associated with each unit is stored by the monitoring system. Each insertion timestamp indicates a time that each unit was inserted into the drilling fluid. A timestamp can be identified by using the mud flowrate and the size of the wellbore. By knowing the volumetric flowrate, diameter of the wellbore, and the length of the well (length and diameter determines volume), an engineer can assign a timestamp to that specific pill and can know when that specific pill should arrive back to the mud return line. From 504, method 500 proceeds to 506.

At 506, continuous images and observed characteristics of returning mud exiting through an annulus of the well and containing the units of smart polymer are captured by a camera positioned at a sensing location and linked to the monitoring system. For example, capturing the continuous images can include capturing, in the units of smart polymers, evidence of pH changes experienced by the units of smart polymers. The sensing location can be, for example, a shale shaker, a centrifuge, a de-sander, or a de-silter. From 506, method 500 proceeds to 508.

At 508, an estimate of pH values at a drill bit of the drilling operation is determined by the monitoring system using the continuous images, the observed characteristics, and the insertion timestamps associated with each unit of smart polymer. Determining the estimate is based at least in part on executing image processing algorithms, machine-learning models, and deep-learning models. As an example, estimating the pH values can include correlating an arrival timestamp identifying a time of arrival of each unit of smart polymer at the sensing location with a respective hole depth by utilizing a rig sensor for mud flow rate and based on an annular area of the well. From 508, method 500 proceeds to 510.

At 510, changes to be made to drilling parameters for the drilling operation are suggested by the monitoring system based at least in part on the estimate of the pH values. For example, the drilling pH can be changed manually by a mud specialist. After 510, method 500 can stop.

In some implementations, in addition to (or in combination with) any previously-described features, techniques of the present disclosure can include the following. Outputs of the techniques of the present disclosure can be performed before, during, or in combination with wellbore operations, such as to provide inputs to change the settings or parameters of equipment used for drilling. Examples of wellbore operations include forming/drilling a wellbore, hydraulic fracturing, and producing through the wellbore, to name a few. The wellbore operations can be triggered or controlled, for example, by outputs of the methods of the present disclosure. In some implementations, customized user interfaces can present intermediate or final results of the above described processes to a user. Information can be presented in one or more textual, tabular, or graphical formats, such as through a dashboard. The information can be presented at one or more on-site locations (such as at an oil well or other facility), on the Internet (such as on a webpage), on a mobile application (or "app"), or at a central processing facility. The presented information can include suggestions, such as suggested changes in parameters or processing inputs, that the user can select to implement improvements in a production environment, such as in the exploration, production, and/or testing of petrochemical processes or facilities. For example, the suggestions can include parameters that, when selected by the user, can cause a change to, or an improvement in, drilling parameters (including drill bit speed and direction) or overall production of a gas or oil well. The suggestions, when implemented by the user, can improve the speed and accuracy of calculations, streamline processes, improve models, and solve problems related to efficiency, performance, safety, reliability, costs, downtime, and the need for human interaction. In some implementations, the suggestions can be implemented in real-time, such as to provide an immediate or near-immediate change in operations or in a model. The term real-time can correspond, for example, to events that occur within a specified period of time, such as within one minute or within one second. Events can include readings or measurements captured by downhole equipment such as sensors, pumps, bottom hole assemblies, or other equipment. The readings or measurements can be analyzed at the surface, such as by using applications that can include modeling applications and machine learning. The analysis can be used to generate changes to settings of downhole equipment, such as drilling equipment. In some implementations, values of parameters or other variables that are determined can be used automatically (such as through using rules) to implement changes in oil or gas well exploration, production/drilling, or testing. For example, outputs of the present disclosure can be used as inputs to other equipment and/or systems at a facility. This can be especially useful for systems or various pieces of equipment that are located several meters or several miles apart, or are located in different countries or other jurisdictions.

Figure 6:
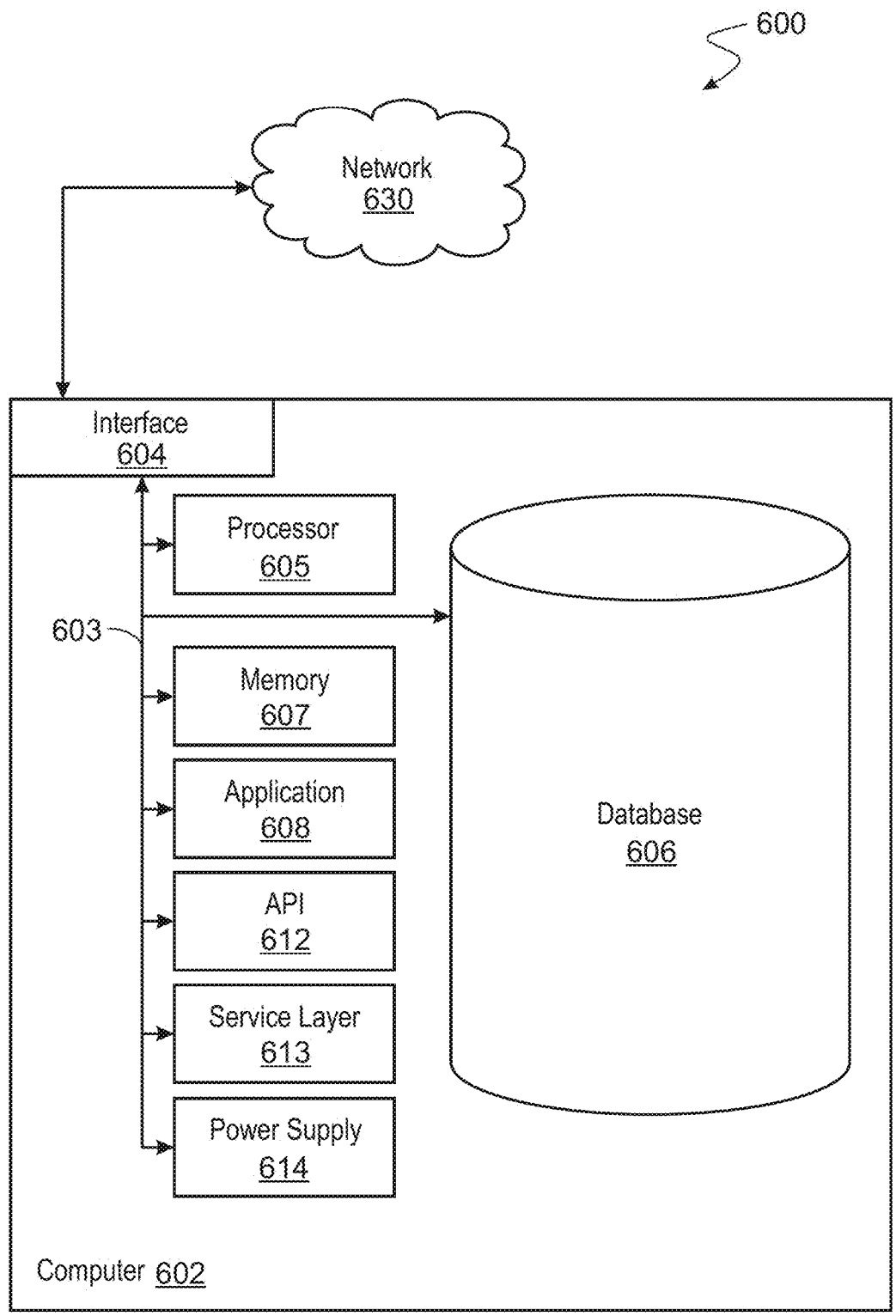
FIG. 6 is a block diagram illustrating an example computer system used to provide computational functionalities associated with described algorithms, methods, functions, processes, flows, and procedures as described in the present disclosure, according to some implementations of the present disclosure.

FIG. 6 is a block diagram of an example computer system 600 used to provide computational functionalities associated with described algorithms, methods, functions, processes, flows, and procedures described in the present disclosure, according to some implementations of the present disclosure. The illustrated computer 602 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 602 can include input devices such as keypads, keyboards, and touch screens that can accept user information. Also, the computer 602 can include output devices that can convey information associated with the operation of the computer 602. The information can include digital data, visual data, audio information, or a combination of information. The information can be presented in a graphical user interface (UI) (or GUI).

The computer 602 can serve in a role as a client, a network component, a server, a database, a persistency, or components of a computer system for performing the subject matter described in the present disclosure. The illustrated computer 602 is communicably coupled with a network 630. In some implementations, one or more components of the computer 602 can be configured to operate within different environments, including cloud-computing-based environments, local environments, global environments, and combinations of environments.

At a top level, the computer 602 is an electronic computing device operable to receive, transmit, process, store, and manage data and information associated with the described subject matter. According to some implementations, the computer 602 can also include, or be communicably coupled with, an application server, an email server, a web server, a caching server, a streaming data server, or a combination of servers.

The computer 602 can receive requests over network 630 from a client application (for example, executing on another computer 602). The computer 602 can respond to the received requests by processing the received requests using software applications. Requests can also be sent to the computer 602 from internal users (for example, from a command console), external (or third) parties, automated applications, entities, individuals, systems, and computers.

Each of the components of the computer 602 can communicate using a system bus 603. In some implementations, any or all of the components of the computer 602, including hardware or software components, can interface with each other or the interface 604 (or a combination of both) over the system bus 603. Interfaces can use an application programming interface (API) 612, a service layer 613, or a combination of the API 612 and service layer 613. The API 612 can include specifications for routines, data structures, and object classes. The API 612 can be either computer-language independent or dependent. The API 612 can refer to a complete interface, a single function, or a set of APIs.

The service layer 613 can provide software services to the computer 602 and other components (whether illustrated or not) that are communicably coupled to the computer 602. The functionality of the computer 602 can be accessible for all service consumers using this service layer. Software services, such as those provided by the service layer 613, can provide reusable, defined functionalities through a defined interface. For example, the interface can be software written in JAVA, C++, or a language providing data in extensible markup language (XML) format. While illustrated as an integrated component of the computer 602, in alternative implementations, the API 612 or the service layer 613 can be stand-alone components in relation to other components of the computer 602 and other components communicably coupled to the computer 602. Moreover, any or all parts of the API 612 or the service layer 613 can be implemented as child or sub-modules of another software module, enterprise application, or hardware module without departing from the scope of the present disclosure.

The computer 602 includes an interface 604. Although illustrated as a single interface 604 in FIG. 6, two or more interfaces 604 can be used according to particular needs, desires, or particular implementations of the computer 602 and the described functionality. The interface 604 can be used by the computer 602 for communicating with other systems that are connected to the network 630 (whether illustrated or not) in a distributed environment. Generally, the interface 604 can include, or be implemented using, logic encoded in software or hardware (or a combination of software and hardware) operable to communicate with the network 630. More specifically, the interface 604 can include software supporting one or more communication protocols associated with communications. As such, the network 630 or the interface's hardware can be operable to communicate physical signals within and outside of the illustrated computer 602.

The computer 602 includes a processor 605. Although illustrated as a single processor 605 in FIG. 6, two or more processors 605 can be used according to particular needs, desires, or particular implementations of the computer 602 and the described functionality. Generally, the processor 605 can execute instructions and can manipulate data to perform the operations of the computer 602, including operations using algorithms, methods, functions, processes, flows, and procedures as described in the present disclosure.

The computer 602 also includes a database 606 that can hold data for the computer 602 and other components connected to the network 630 (whether illustrated or not). For example, database 606 can be an in-memory, conventional, or a database storing data consistent with the present disclosure. In some implementations, database 606 can be a combination of two or more different database types (for example, hybrid in-memory and conventional databases) according to particular needs, desires, or particular implementations of the computer 602 and the described functionality. Although illustrated as a single database 606 in FIG. 6, two or more databases (of the same, different, or combination of types) can be used according to particular needs, desires, or particular implementations of the computer 602 and the described functionality. While database 606 is illustrated as an internal component of the computer 602, in alternative implementations, database 606 can be external to the computer 602.

The computer 602 also includes a memory 607 that can hold data for the computer 602 or a combination of components connected to the network 630 (whether illustrated or not). Memory 607 can store any data consistent with the present disclosure. In some implementations, memory 607 can be a combination of two or more different types of memory (for example, a combination of semiconductor and magnetic storage) according to particular needs, desires, or particular implementations of the computer 602 and the described functionality. Although illustrated as a single memory 607 in FIG. 6, two or more memories 607 (of the same, different, or combination of types) can be used according to particular needs, desires, or particular implementations of the computer 602 and the described functionality. While memory 607 is illustrated as an internal component of the computer 602, in alternative implementations, memory 607 can be external to the computer 602.

The application 608 can be an algorithmic software engine providing functionality according to particular needs, desires, or particular implementations of the computer 602 and the described functionality. For example, application 608 can serve as one or more components, modules, or applications. Further, although illustrated as a single application 608, the application 608 can be implemented as multiple applications 608 on the computer 602. In addition, although illustrated as internal to the computer 602, in alternative implementations, the application 608 can be external to the computer 602.

The computer 602 can also include a power supply 614. The power supply 614 can include a rechargeable or non-rechargeable battery that can be configured to be either user- or non-user-replaceable. In some implementations, the power supply 614 can include power-conversion and management circuits, including recharging, standby, and power management functionalities. In some implementations, the power supply 614 can include a power plug to allow the computer 602 to be plugged into a wall socket or a power source to, for example, power the computer 602 or recharge a rechargeable battery.

There can be any number of computers 602 associated with, or external to, a computer system containing computer 602, with each computer 602 communicating over network 630. Further, the terms "client," "user," and other appropriate terminology can be used interchangeably, as appropriate, without departing from the scope of the present disclosure. Moreover, the present disclosure contemplates that many users can use one computer 602 and one user can use multiple computers 602.

Described implementations of the subject matter can include one or more features, alone or in combination.

For example, in a first implementation, a computer-implemented method includes the following. Units of smart polymers with per-hydrogen (pH) sensitivity are inserted by a monitoring system into drilling fluid pumped into a well during a drilling operation. The smart polymers are configured to be triggered by hydrogen ion concentrations. An insertion timestamp associated with each unit is stored by the monitoring system. Each insertion timestamp indicates a time that each unit was inserted into the drilling fluid. Continuous images and observed characteristics of returning mud exiting through an annulus of the well and containing the units of smart polymer are captured by a camera positioned at a sensing location and linked to the monitoring system. An estimate of pH values at a drill bit of the drilling operation is determined by the monitoring system using the continuous images, the observed characteristics, and the insertion timestamps associated with each unit of smart polymer. Determining the estimate is based at least in part on executing image processing algorithms, machine-learning models, and deep-learning models. Changes to be made to drilling parameters for the drilling operation are suggested by the monitoring system based at least in part on the estimate of the pH values.

The foregoing and other described implementations can each, optionally, include one or more of the following features:

A first feature, combinable with any of the following features, where the units of smart polymers have a pill shape.

A second feature, combinable with any of the previous or following features, where the method further includes pumping the units of smart polymers into the drilling fluid at different intervals or every one stand.

A third feature, combinable with any of the previous or following features, where the units of smart polymers are configured to change properties as a function of exposure to different hydrogen ion [$H^+$] concentrations applied to the units of smart polymers by downhole conditions.

A fourth feature, combinable with any of the previous or following features, where capturing the continuous images includes capturing, in the units of smart polymers, evidence of pH changes experienced by the units of smart polymers.

A fifth feature, combinable with any of the previous or following features, where estimating the pH values includes correlating an arrival timestamp identifying a time of arrival of each unit of smart polymer at the sensing location with a respective hole depth by utilizing a rig sensor for mud flow rate and based on an annular area of the well.

A sixth feature, combinable with any of the previous or following features, where the sensing location is selected from the group consisting of a shale shaker, a centrifuge, a de-sander, and a de-silter.

In a second implementation, a non-transitory, computer-readable medium stores one or more instructions executable by a computer system to perform operations including the following. Units of smart polymers with per-hydrogen (pH) sensitivity are inserted by a monitoring system into drilling fluid pumped into a well during a drilling operation. The smart polymers are configured to be triggered by hydrogen ion concentrations. An insertion timestamp associated with each unit is stored by the monitoring system. Each insertion timestamp indicates a time that each unit was inserted into the drilling fluid. Continuous images and observed characteristics of returning mud exiting through an annulus of the well and containing the units of smart polymer are captured by a camera positioned at a sensing location and linked to the monitoring system. An estimate of pH values at a drill bit of the drilling operation is determined by the monitoring system using the continuous images, the observed characteristics, and the insertion timestamps associated with each unit of smart polymer. Determining the estimate is based at least in part on executing image processing algorithms, machine-learning models, and deep-learning models. Changes to be made to drilling parameters for the drilling operation are suggested by the monitoring system based at least in part on the estimate of the pH values.

The foregoing and other described implementations can each, optionally, include one or more of the following features:

A first feature, combinable with any of the following features, where the units of smart polymers have a pill shape.

A second feature, combinable with any of the previous or following features, where the operations further include pumping the units of smart polymers into the drilling fluid at different intervals or every one stand.

A third feature, combinable with any of the previous or following features, where the units of smart polymers are configured to change properties as a function of exposure to different hydrogen ion [$H^+$] concentrations applied to the units of smart polymers by downhole conditions.

A fourth feature, combinable with any of the previous or following features, where capturing the continuous images includes capturing, in the units of smart polymers, evidence of pH changes experienced by the units of smart polymers.

A fifth feature, combinable with any of the previous or following features, where estimating the pH values includes correlating an arrival timestamp identifying a time of arrival of each unit of smart polymer at the sensing location with a respective hole depth by utilizing a rig sensor for mud flow rate and based on an annular area of the well.

A sixth feature, combinable with any of the previous or following features, where the sensing location is selected from the group consisting of a shale shaker, a centrifuge, a de-sander, and a de-silter.

In a third implementation, a computer-implemented system includes one or more processors and a non-transitory computer-readable storage medium coupled to the one or more processors and storing programming instructions for execution by the one or more processors. The programming instructions instruct the one or more processors to perform operations including the following. Units of smart polymers with per-hydrogen (pH) sensitivity are inserted by a monitoring system into drilling fluid pumped into a well during a drilling operation. The smart polymers are configured to be triggered by hydrogen ion concentrations. An insertion timestamp associated with each unit is stored by the monitoring system. Each insertion timestamp indicates a time that each unit was inserted into the drilling fluid. Continuous images and observed characteristics of returning mud exiting through an annulus of the well and containing the units of smart polymer are captured by a camera positioned at a sensing location and linked to the monitoring system. An estimate of pH values at a drill bit of the drilling operation is determined by the monitoring system using the continuous images, the observed characteristics, and the insertion timestamps associated with each unit of smart polymer. Determining the estimate is based at least in part on executing image processing algorithms, machine-learning models, and deep-learning models. Changes to be made to drilling parameters for the drilling operation are suggested by the monitoring system based at least in part on the estimate of the pH values.

The foregoing and other described implementations can each, optionally, include one or more of the following features:

A first feature, combinable with any of the following features, where the units of smart polymers have a pill shape.

A second feature, combinable with any of the previous or following features, where the operations further include pumping the units of smart polymers into the drilling fluid at different intervals or every one stand.

A third feature, combinable with any of the previous or following features, where the units of smart polymers are configured to change properties as a function of exposure to different hydrogen ion [$H^+$] concentrations applied to the units of smart polymers by downhole conditions.

A fourth feature, combinable with any of the previous or following features, where capturing the continuous images includes capturing, in the units of smart polymers, evidence of pH changes experienced by the units of smart polymers.

A fifth feature, combinable with any of the previous or following features, where estimating the pH values includes correlating an arrival timestamp identifying a time of arrival of each unit of smart polymer at the sensing location with a respective hole depth by utilizing a rig sensor for mud flow rate and based on an annular area of the well.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to a suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatuses, devices, and machines for processing data, including by way of example, a programmable processor, a computer, or multiple processors or computers. The apparatus can also include special purpose logic circuitry including, for example, a central processing unit (CPU), a field-programmable gate array (FPGA), or an application-specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, such as LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub-programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory.

Graphics processing units (GPUs) can also be used in combination with CPUs. The GPUs can provide specialized processing that occurs in parallel to processing performed by CPUs. The specialized processing can include artificial intelligence (AI) applications and processing, for example. GPUs can be used in GPU clusters or in multi-GPU computing.

A computer can include, or be operatively coupled to, one or more mass storage devices for storing data. In some implementations, a computer can receive data from, and transfer data to, the mass storage devices including, for example, magnetic, magneto-optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer-readable media (transitory or non-transitory, as appropriate) suitable for storing computer program instructions and data can include all forms of permanent/non-permanent and volatile/non-volatile memory, media, and memory devices. Computer-readable media can include, for example, semiconductor memory devices such as random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer-readable media can also include, for example, magnetic devices such as tape, cartridges, cassettes, and internal/removable disks. Computer-readable media can also include magneto-optical disks and optical memory devices and technologies including, for example, digital video disc (DVD), CD-ROM, DVD+/−R, DVD-RAM, DVD-ROM, HD-DVD, and BLU-RAY.

The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated into, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that the user uses. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch-screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at the application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations. It should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system including a computer memory interoperably coupled with a hardware processor configured to perform the computer-implemented method or the instructions stored on the non-transitory, computer-readable medium.

What is claimed is:

1. A computer-implemented method, comprising:
   inserting, by a monitoring system, units of smart polymers with per-hydrogen (pH) sensitivity into drilling fluid pumped into a well during a drilling operation, the smart polymers configured to be triggered by hydrogen ion concentrations;
   storing, by the monitoring system, an insertion timestamp associated with each unit, each insertion timestamp indicating a time that each unit was inserted into the drilling fluid;
   capturing, by a camera positioned at a sensing location and linked to the monitoring system, continuous images and observed characteristics of returning mud exiting through an annulus of the well and containing the units of smart polymer;
   determining, by the monitoring system and using the continuous images and the observed characteristics and the insertion timestamps associated with each unit of smart polymer, an estimate of pH values at a drill bit of the drilling operation, wherein determining the estimate is based at least in part on executing image processing algorithms, machine-learning models, and deep-learning models; and
   suggesting, by the monitoring system and based at least in part on the estimate of the pH values, changes to be made to drilling parameters for the drilling operation.

2. The computer-implemented method of claim 1, wherein the units of smart polymers have a pill shape.

3. The computer-implemented method of claim 1, further comprising:
   pumping the units of smart polymers into the drilling fluid at different intervals or every one stand.

4. The computer-implemented method of claim 1, wherein the units of smart polymers are configured to change properties as a function of exposure to different hydrogen ion [$H^+$] concentrations applied to the units of smart polymers by downhole conditions.

5. The computer-implemented method of claim 1, wherein capturing the continuous images includes capturing, in the units of smart polymers, evidence of pH changes experienced by the units of smart polymers.

6. The computer-implemented method of claim 1, wherein estimating the pH values includes correlating an arrival timestamp identifying a time of arrival of each unit of smart polymer at the sensing location with a respective hole depth by utilizing a rig sensor for mud flow rate and based on an annular area of the well.

7. The computer-implemented method of claim 1, wherein the sensing location is selected from the group consisting of a shale shaker, a centrifuge, a de-sander, and a de-silter.

\* \* \* \* \*